US008114901B2

(12) United States Patent
Bush et al.

(10) Patent No.: US 8,114,901 B2
(45) Date of Patent: Feb. 14, 2012

(54) CRYSTALLINE 2,5-DIONE-3-(1-METHYL-1H-INDOL-3-YL)-4-[1-(PYRIDIN-2-YLMETHYL)PIPERIDIN-4-YL]-1H-INDOL-3-YL]-1H-PYRROLE MONO-HYDROCHLORIDE

(75) Inventors: Julie Kay Bush, Fishers, IN (US); Margaret Mary Faul, Zionsville, IN (US); Susan Marie Reutzel-Edens, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 848 days.

(21) Appl. No.: 10/520,360

(22) PCT Filed: Jul. 8, 2003

(86) PCT No.: PCT/US03/19548
§ 371 (c)(1),
(2), (4) Date: Jan. 5, 2005

(87) PCT Pub. No.: WO2004/006928
PCT Pub. Date: Jan. 22, 2004

(65) Prior Publication Data
US 2005/0288332 A1    Dec. 29, 2005

Related U.S. Application Data

(60) Provisional application No. 60/395,976, filed on Jul. 12, 2002.

(51) Int. Cl.
*A61K 31/41* (2006.01)
*A61K 31/40* (2006.01)
*C07D 209/02* (2006.01)
*C07D 209/00* (2006.01)

(52) U.S. Cl. ......... 514/414; 548/455; 548/466; 548/468

(58) Field of Classification Search ................... 540/479; 546/94, 201, 466; 514/414; 548/455, 466, 548/468
See application file for complete search history.

(56) References Cited

U.S. PATENT DOCUMENTS

| | | | |
|---|---|---|---|
| 4,785,085 A | 11/1988 | Kaneko et al. | |
| 4,808,613 A | 2/1989 | Kaneko et al. | |
| 4,855,489 A | 8/1989 | Trostmann et al. | |
| 4,923,986 A | 5/1990 | Murakata et al. | |
| 5,057,614 A | 10/1991 | Davis et al. | |
| 5,292,747 A | 3/1994 | Davis et al. | |
| 5,380,746 A | 1/1995 | Barth et al. | |
| 5,481,003 A | 1/1996 | Gillig et al. | |
| 5,489,608 A | 2/1996 | Kleinschroth et al. | |
| 5,516,915 A | 5/1996 | Barth et al. | |
| 5,545,636 A * | 8/1996 | Heath et al. | 514/214.02 |
| 5,552,396 A | 9/1996 | Heath, Jr. et al. | |
| 5,668,152 A * | 9/1997 | Heath et al. | 514/323 |
| 5,672,618 A * | 9/1997 | Heath et al. | 514/414 |
| 5,721,245 A | 2/1998 | Davis et al. | |
| 6,407,058 B1 | 6/2002 | Staddon et al. | |
| 6,987,110 B2 * | 1/2006 | Zhang et al. | 514/252.1 |

FOREIGN PATENT DOCUMENTS

| | | |
|---|---|---|
| EP | 0 269 025 A2 | 11/1987 |
| EP | 0 328 000 A2 | 2/1989 |
| EP | 0 397 060 A2 | 5/1990 |
| EP | 0 470 490 A1 | 7/1991 |
| EP | 0 540 956 A1 | 10/1992 |
| EP | 0 624 586 A1 | 11/1994 |
| WO | WO 91/13070 | 9/1991 |
| WO | WO 91/13071 | 9/1991 |
| WO | WO 94/02488 | 2/1994 |
| WO | WO 94/14798 | 7/1994 |
| WO | WO 95/09843 | 4/1995 |
| WO | WO 95/17182 | 6/1995 |
| WO | 9804551 A1 | 2/1998 |
| WO | WO 01/30331 A2 | 5/2001 |
| WO | WO 02/02094 A2 | 1/2002 |
| WO | WO 02/02116 A2 | 1/2002 |

OTHER PUBLICATIONS

Vippagunta et al. (Advanced Drug Delivery Reviews 48, (2001), 3-26).*
Derwent Abstract 90-132947/18; 21.10.88-DE-835842.
Derwent Abstract 92-274042/33; 90.11.20 90JP-314628.
Meier, et al., *Tetrahedron Letters*, 34:33, 5277-5280 (1993).
Wilkinson, et al., *Bichem. J.*, 294, 335-337 (1993).
Bit, et al., *J. Med. Chem.*, 36, 21-29 (1993).
Martiny-Baron, et al., *The Journal of Biological Chemistry*, 268:13, 9194-9197 (1993).
Krakowiak, et al., *SYNLETT*, 611-620, (Sep. 1993).
Mulqueen, et al., *Agents Actions*, 37, 85-89 (1992).
Davis, et al., *J. Med. Chem.*, 35, 177-184 (1992).
Davis, et al., *J. Med. Chem.*, 35, 994-1001 (1992).
Toullec, et al., *The Journal of Biological Chemistry*, 266:24, 15771-15781 (1991).
Nixon, et al., *Drugs Exptl. Clin. Res.*, 17:8, 389-393 (1991).
Davis, et al., *Tetrahedron Letters*, 31:36, 5201-5204 (1990).
Brenner, et al., *Tetrahedron Letters*, 44:10, 2887-2892 (1988).
Joyce, et al., *The Journal of Organic Chemistry*, 52:7, 1177-1186 (1987).
Buchdunger, et al., *Proc. Natl. Acad. Sci. USA*, 91, 2334-2338 (Mar. 1994).
Kobayashi, et al., *The American Physiological Society*, 0363-6135, H1214-H1220 (1994).
Felsenstein, et al., *Neuroscience Letters*, 174, 173-176 (1994).
Demaerschalck, et al., *Biochimca et Biophysica Acta*, 1181, 214-218 (1993).
Shimohama, et al., *Neurology*, 43, 1407-1413 (1993).

(Continued)

*Primary Examiner* — Sabiha Qazi
(74) *Attorney, Agent, or Firm* — Tina M. Tucker; Gilbert Voy; John A. Cleveland, Jr.

(57) ABSTRACT

The present invention relates to crystalline 2,5-dione-3-(1-methyl-1H-indol-3-yl)-4-[1-(pyridin-2-yl-methyl)piperidin-4-yl]-1H-indol-3-yl]-1H-pyrrole mono-hydrochloride salt, a pharmaceutical formulation containing said salt and to methods for treating cancer and for inhibiting tumor growth using said salt.

2 Claims, 1 Drawing Sheet

OTHER PUBLICATIONS

Bradshaw, et al., *Agents Actions*, 38, 135-147 (1993).
Ishii, et al., *Science*, 272, 728-731 (May 3, 1996).
Correspondence between CAS Client Services, Dr. Margaret Faul, and Ms. Marie Cable regarding Order No. 63919, Registry Nos. 359017-72-4 and 359017-79-1; dated Sep. 28, 2001 and Sep. 25, 2001.
Beckage, Michael, et al., "Physical Characterization of LY317615 (PKC II): A Di-Hcl to Mono-Hcl Salt Conversion on Heating and Precipitation," PPD Technical Report (1999).
Collins, David, et al., "Biopharmaceutics properties and salt selection for the PKC-beta inhibitor LSN 317615," PPD Technical Report (2000).

\* cited by examiner

CRYSTALLINE 2,5-DIONE-3-(1-METHYL-1H-INDOL-3-YL)-4-[1-(PYRIDIN-2-YLMETHYL)PIPERIDIN-4-YL]-1H-INDOL-3-YL]-1H-PYRROLE MONO-HYDROCHLORIDE

This application claims the benefit under 35 U.S.C. §120 of International Application No. PCT/US2003/19548 filed Jul. 8, 2003, which claims the benefit under 35 U.S.C. §119(e) of U.S. Ser. No. 60/395,976, filed Jul. 12, 2002.

BACKGROUND OF THE INVENTION

Compounds of formula I:

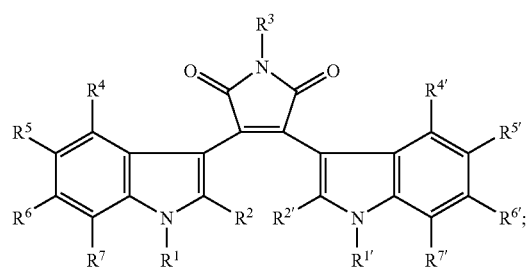

and pharmaceutically acceptable salts thereof, useful as protein kinase C inhibitors, were disclosed by Heath, et al., in European Patent Publication No. 817,627 (Heath).

Example #49 of Heath disclosed a free base compound of formula FB:

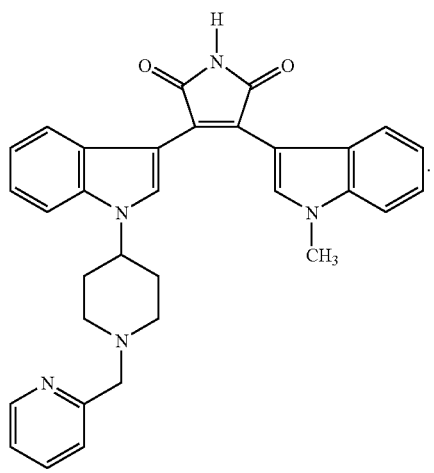

While FB is undoubtedly a very effective pharmaceutical agent, unexpected difficulties were encountered in its large-scale production. Thus, unpredictable formation of solvates complicated the commercial synthesis to such an extent that it became necessary to develop an alternative form for large-scale commercialization.

In this context, WO 02/02094 and WO 02/02116 specifically describe the use of the dihydrochloride salt of FB (FB-2HCl) to treat cancer and to inhibit tumor growth as a monotherapy or in conjunction with an anti-neoplastic agent or radiation therapy. Unfortunately, it has now been determined that FB-2HCl is hygroscopic. In addition, although FB-2HCl appears to be crystalline by optical light microscopy, more detailed study by X-ray powder diffraction (XRD) has revealed that this material is in fact only poorly crystalline.

Surprisingly, in accordance with the invention, it has now been discovered that the monohydrochloride salt of FB is capable of being reproducibly produced on a commercial scale, is not significantly hygroscopic, is sufficiently stable for use in oral formulations, and can be produced in a highly crystalline state.

BRIEF SUMMARY OF THE INVENTION

The present invention relates to crystalline 2,5-dione-3-(1-methyl-1H-indol-3-yl)-4-[1-(pyridin-2-ylmethyl)piperidin-4-yl]-1H-indol-3-yl]-1H-pyrrole mono-hydrochloride, a hydrate thereof, or mixtures thereof.

The present invention further relates to crystalline 2,5-dione-3-(1-methyl-1H-indol-3-yl)-4-[1-(pyridin-2-ylmethyl)piperidin-4-yl]-1H-indol-3-yl]-1H-pyrrole mono-hydrochloride, a hydrate thereof, or mixtures thereof, having an X-ray diffraction pattern which comprises the following peaks: 6.8±0.1, 10.9±0.1, 14.2±0.1 and 16.6±0.1° in 2θ; when the pattern is obtained from a copper radiation source (CuKα; λ=1.54056 Å). This crystalline material is hereafter referred to as "F-I".

The present invention also relates to a pharmaceutical composition containing F-I and a pharmaceutical carrier. In another embodiment, the pharmaceutical formulation of the present invention may be adapted for use in treating cancer and for use in inhibiting tumor growth.

Moreover, the present invention relates to methods for treating cancer and to methods for inhibiting tumor growth which comprise administering to a mammal in need thereof an effective amount of F-I.

In addition, the present invention is related to F-I for treating cancer and for inhibiting tumor growth.

Another embodiment of the invention provides for the use of F-I for the manufacture of a medicament for the treatment of cancer and for the manufacture of a medicament for inhibiting tumor growth.

DETAILED DESCRIPTION OF THE INVENTION

Figure 1:
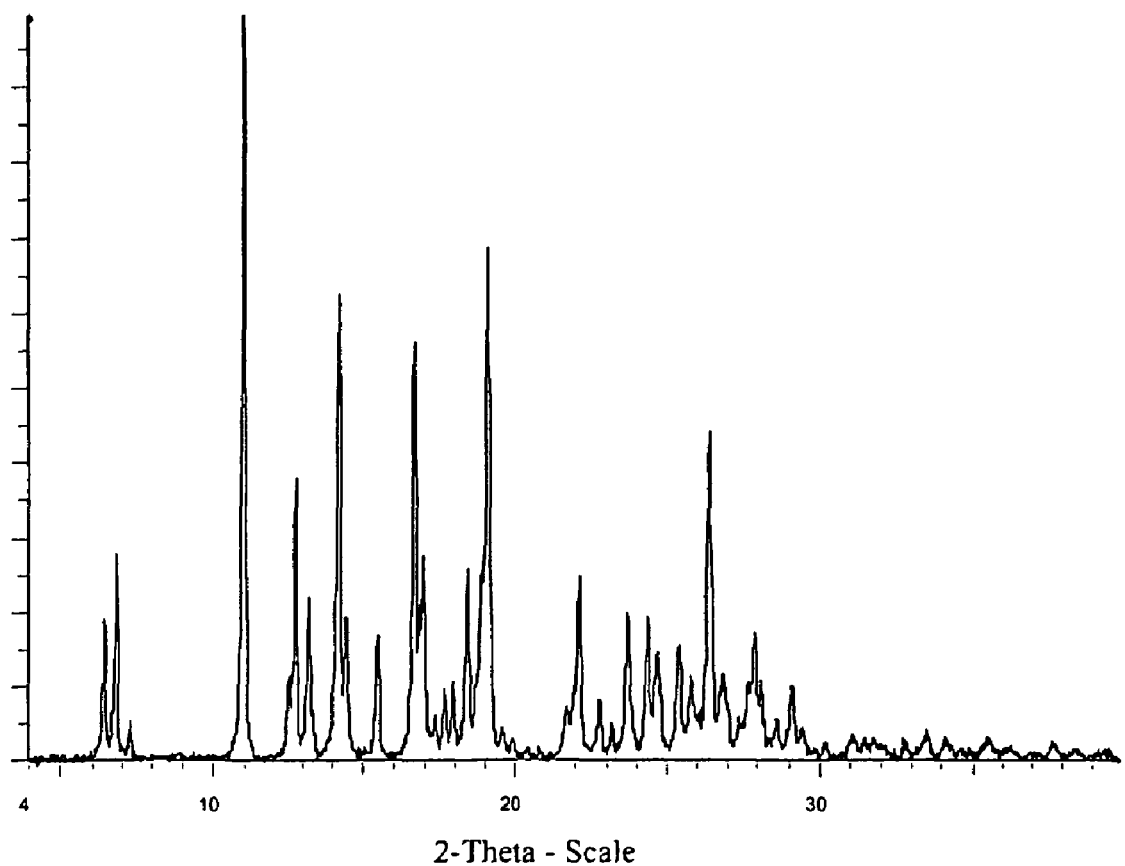
FIG. 1 is a representative XRD pattern for F-I.

Prior to discovering the problems associated with the large-scale manufacturability of FB, due to a concern that FB may not possess optimal bioavailability properties, an in situ salt screen was performed to identify salts for FB possessing improved properties. This screen evaluates the solubility of salts formed in situ in aqueous media. The solubility obtained in situ for a given salt is not directly predictive of the equilibrium solubility of the crystalline form(s) of the same salt. However, the in situ screen can be used to prioritize the salts for synthesis and characterization during salt selection. From these data, five out of seventeen mono-acid salts were chosen for synthesis and characterization. These salts were the citrate, methanesulfonate (mesylate), phosphate, tartrate and mono-hydrochloride (FB-HCl). In addition, FB-2HCl was also synthesized, characterized and analyzed. Some of these salts' properties as well as those of FB are discussed below.

Citrate, Mesylate, Phosphate and Tartrate

The citrate salt generated from methanol is insoluble in water. The mesylate salt is hygroscopic, exhibiting up to 2% weight gain at 70% RH and over 15% weight gain at 95% RH.

Although the phosphate salt exhibits rapid dissolution and high solubility at early time points, the solubility of the phosphate drops to 71 μg/mL upon prolonged incubation. The phosphate salt is also somewhat hygroscopic and exhibited hysteresis in water desorption, indicating possible hydrate formation.

The tartrate is only slightly hygroscopic, exhibiting ~1% weight gain at RH's up to 70%. Based on this and other promising initial results, the tartrate was subjected to a brief polymorph/solvate screen to determine its suitability for bulk manufacturing and use as a pharmaceutical.

The tartrate salt was initially isolated (by titration of the free base with tartaric acid) as a crystalline hydrate. The hydrated material was then recrystallized to determine if other pharmaceutically relevant crystal forms of the tartrate salt could be prepared. The number of solvents suitable for recrystallization was limited by the relatively poor solubility of this salt in many solvents, including polar, protic solvents ($H_2O$, methanol, ethanol and isopropyl alcohol) and many non-protic solvents (acetone, ethyl acetate, methyl ethyl ketone and tetrahydrofuran). Sufficient solubility was observed only in dimethylformamide, dimethylsulfoxide and organic (and organic/aqueous) mixtures. Elevated temperatures were often required to achieve dissolution.

The tartrate salt was typically not generated from the recrystallization experiments that were carried out. Instead, a crystal form of FB was obtained most often. A non-solvated form of the tartrate was not found. These results suggest that isolation of a tartrate salt of FB could be difficult, presumably due to the low solubility of different crystal forms of FB relative to the tartrate salt, and the relatively small difference in pKa between FB and tartaric acid.

FB-2HCl

The aqueous solubility of FB-2HCl under various conditions was analyzed and at concentrations up to 10 mg/mL, solutions of FB-2HCl are stable at ambient temperature for up to 10 days. However, solutions held at 50° C. exhibited profound precipitation prior to the first time point (6 days). At concentrations ≧40 mg/mL, rapid precipitation within minutes was noted at ambient room temperature. XRD analysis and ion chromatography (to determine chloride content) of the precipitated crystals confirmed that this precipitate was FB-HCl.

FB

The product of the synthesis described below in Preparation 1, is typically a non-solvated crystalline form of FB. This non-solvated form (hereafter referred to as FB Form I) is preferred as it crystallizes well in the reaction, filters rapidly and affords a high purity of product (total related substances (TRS) ~0.77%). However, under these very same reaction conditions, a solvate containing tetrahydrofuran (THF) is also sometimes isolated (frequency of occurrence ~10-20%). This crystalline solvate filters very slowly and traps certain impurities resulting in a higher TRS for product (2.42-4.78%). The high TRS associated with this solvate has required that, when present, the isolated solvate be reworked. Despite significant research, the reason for the occasional formation of the solvate containing THF is unknown. The lack of control in preparation of FB Form I has limited its potential for development as the final active pharmaceutical ingredient (API).

FB-HCl

FB-HCl, prepared via addition of 1 equivalent of concentrated or 1N hydrochloric acid to a mixture of FB in a lower alcohol, e.g., methanol, isopropanol or 2-butanol, or in mixture of a lower alcohol and water, is crystalline and has a melting onset temperature of about 256° C. as measured by differential scanning calorimetry (DSC). FB-HCl, produced as described in Example 1, is relatively non-hygroscopic between 0-70% RH (<2% wt gain @95% RH).

Characterization of FB-HCl

Various methods, including thermogravimetric analysis (TGA), DSC and XRD were used to characterize FB-HCl. TGA allows for measurement of the amount and rate of weight change as a function of temperature. TGA is most commonly used to study desolvation processes and to quantitatively determine the total volatile content of a solid. DSC is a technique that is often used to screen compounds for polymorphism because the temperatures(s) at which a physical change in a material occurs is usually characteristic of that material. DSC is often used to complement TGA analysis in screening compounds for physical changes upon controlled heating. XRD is a technique that detects long-range order in a crystalline material and can be performed at different RH's to detect subtle phase changes induced by moisture sorption.

Different lots of FB-HCl, prepared via addition of 1 equivalent of concentrated or 1 N hydrochloric acid to a mixture of FB in methanol, were analyzed by TGA and were found to retain different levels of water: from <0.01% (anhydrous material) all the way to 1.6% (hemi-hydrate). The TGA results showed not only the different amounts of water present in the crystalline FB-HCl materials, but also that the water, when present, is readily expelled from the material upon heating above ambient temperature.

The different water contents prompted an investigation into the moisture sorption characteristics of those lots of crystalline FB-HCl that were not anhydrous. Indeed, the various partially hydrated lots showed distinctly different water uptake profiles. Regardless of the amount of water sorbed in the crystalline FB-HCl lattice, the sorption isotherms consistently showed gradual weight gains up to ~40% RH, above which, the water uptake plateaued. The maximum moisture sorption (1.6% at 40% RH) observed for those partially hydrated lots of crystalline FB-HCl suggests that at full water occupancy, a hemihydrate (0.5 mole) composition is present. Crystalline FB-HCl material capable of water sorption is hereafter referred to as "hygroscopic F-I".

The XRD peaks of hygroscopic F-I did not shift at any RH. The XRD patterns generated for hygroscopic F-I were identical to XRD patterns generated for the non-hygroscopic F-I material (hereafter referred to as "anhydrous F-I"). The absence of changes to the XRD pattern when moving from anhydrous F-I to hygroscopic F-I, as well as the absence of changes to the XRD pattern for hygroscopic F-I as a function of humidity, shows not only that the crystal lattice of F-I is unperturbed by the moisture sorption process, but also that moisture sorption into the particles cannot be site-specific.

F-I (both hygroscopic and anhydrous) exhibits a strong, unique XRD pattern with sharp peaks and a flat baseline, indicative of a highly crystalline material (see FIG. 1). The angular peak positions in 2θ and corresponding $I/I_o$ data for all F-I peaks with intensities equal to or greater than 5% of the largest peak are tabulated in Table 1. All data in Table 1 is expressed with an accuracy of ±0.1° in 2θ.

TABLE 1

| Angle 2θ | $I/I_o$ (%) |
|---|---|
| 6.3 | 19.1 |
| 6.8 | 27.8 |
| 7.2 | 5.0 |
| 10.9 | 100 |
| 12.5 | 11.2 |
| 12.7 | 38.0 |
| 13.2 | 21.0 |

TABLE 1-continued

| Angle 2θ | I/I$_o$ (%) |
|---|---|
| 14.2 | 62.6 |
| 14.4 | 19.1 |
| 15.4 | 17.0 |
| 16.6 | 56.3 |
| 16.8 | 21.8 |
| 17.0 | 27.2 |
| 17.3 | 5.9 |
| 17.7 | 9.6 |
| 17.9 | 10.4 |
| 18.4 | 25.8 |
| 18.8 | 24.5 |
| 19.1 | 69.1 |
| 21.7 | 7.3 |
| 22.1 | 24.8 |
| 22.8 | 7.9 |
| 23.7 | 19.7 |
| 24.4 | 19.1 |
| 24.7 | 14.4 |
| 25.4 | 15.5 |
| 25.8 | 11.3 |
| 26.4 | 44.1 |
| 26.8 | 11.6 |
| 27.7 | 10.7 |
| 27.9 | 17.1 |
| 28.1 | 10.8 |
| 28.6 | 5.3 |
| 29.1 | 9.7 |

It is well known in the crystallography art that, for any given crystal form, the relative intensities of the diffraction peaks may vary due to preferred orientation resulting from factors such as crystal morphology. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that, for any given crystal form, the angular peak positions may vary slightly. For example, peak positions can shift due to a variation in the temperature at which a sample is analyzed, sample displacement, or the presence or absence of an internal standard. In the present case, a peak position variability of ±0.1° in 2θ will take into account these potential variations without hindering the unequivocal identification of a crystalline salt of the present invention.

A well-known and accepted method for searching crystal forms in the literature is the "Fink" method. The Fink method uses the four most intense lines for the initial search followed by the next four most intense lines. In general accord with the Fink method, based on peak intensities as well as peak position, F-I may be identified by the presence of peaks at 6.8±0.1, 10.9±0.1, 14.2±0.1 and 16.6±0.1° in 2θ; when the pattern is obtained from a copper radiation source (λ=1.54056). The presence of F-I may be further verified by peaks at 6.3±0.1, 7.2±0.1, 12.5±0.1, and 17.0±0.1° in 2θ; when the pattern is obtained from a copper radiation source (λ=1.54056).

FB Form I vs. hygroscopic F-J vs. anhydrous F-I

Extensive equilibrium solubility determinations were undertaken for both hygroscopic and anhydrous F-I in a variety of aqueous media at ambient temperature. Additionally, the equilibrium solubility of FB Form I was measured at ambient temperature. Samples were assayed by high performance liquid chromatography (HPLC) after 24 hours of equilibration in the respective solvents. The results are summarized in Table 2.

TABLE 2

| Sample | Solvent | Amt Dissolved (mg/mL) | Filtrate pH |
|---|---|---|---|
| FB Form I | 0.01 N HCl | 0.279, 0.355 | 2.20 |
| Anhydrous F-I | | 0.054, 0.056 | 2.19 |
| Hygroscopic F-I | | 0.046, 0.053 | 2.25 |
| FB Form I | pH 2.2 buffer | 0.346, 0.336 | 2.21 |
| Anhydrous F-I | | 0.360, 0.363 | 2.27 |
| Hygroscopic F-I | | 0.324, 0.352 | 2.26 |
| FB Form I | SIF, fed pH 5.0 | 0.073, 0.074 | 4.94 |
| Anhydrous F-I | | 0.016, 0.015 | 4.94 |
| Hygroscopic F-I | | 0.014, 0.015 | 4.93 |

The equilibrium solubility data reveal that while F-I (hygroscopic and anhydrous) and FB Form I have similar solubilities in pH 2.2 buffer, F-I is significantly less soluble than FB Form I in 0.01N HCl and simulated intestinal fluid (SIF) (fed). No significant differences between hygroscopic and anhydrous F-I in any media tested were observed.

The solubility results suggest that controlling the bulk composition (hygroscopic vs. anhydrous particles) of F-I as an API is not critical from a bioavailability standpoint. To confirm that variability in the hygroscopicity of F-I lots should not adversely impact bioavailability, intrinsic dissolution rates were also measured for the hygroscopic and anhydrous F-I. For comparison purposes, the intrinsic dissolution rate of FB Form I was also measured. Because FB Form I dissolved too rapidly (>10% of a 100 mg compact dissolved within 10 minutes) and the hygroscopic and anhydrous F-I dissolved too slowly (no appreciable dissolution in 10 minutes), precise intrinsic dissolution rates could not be determined. The intrinsic dissolution results are summarized in Table 3.

TABLE 3

| | % of 100 mg Compact Dissolved in 10 Minutes | | |
|---|---|---|---|
| Dissolution Medium | Hygroscopic F-I | Anhydrous F-1 | FB Form I |
| 0.1 N HCl | <<0.5 | <<0.5 | >30 |

The in vitro dissolution and solubility data discussed above suggest that FB Form I should offer bioavailability advantages in vivo relative to F-I. In order to confirm this prediction, the plasma pharmacokinetic parameters of FB Form I in fed female beagle dogs were evaluated following single oral administration by gavage of 5 mg/kg of FB Form I or F-I in a cross-over design. The 6 dogs were randomized into two treatment groups to receive single doses of FB Form I followed by a single dose of F-I two weeks later, or vice versa. On Days 1 and 14, 3 dogs received FB Form 1 and 3 dogs received F-I, and blood samples were collected at 0.5, 1, 2, 3, 4, 8, 12 and 24 hours post dosing. Concentrations of FB Form I were determined by liquid chromatography tandem mass spectrometry. These concentrations were subsequently used to determine the pharmacokinetic parameters reported in Table 4.

TABLE 4

| Animal | Dosing Regimen | Cmax (nM) FB Form I | Cmax (nM) F-I | AUC0-24 (nM × hr) FB Form I | AUC0-24 (nM × hr) F-I | AUC0-inf (nM × hr) FB Form I | AUC0-inf (nM × hr) F-I |
|---|---|---|---|---|---|---|---|
| 1 | 1 | 531.6 | 679.0 | 2092.4 | 2970.0 | 2113.9 | 3016.1 |
| 2 | 1 | 600.2 | 501.4 | 3477.5 | 4064.4 | 3603.1 | 4200.8 |
| 3 | 1 | 552.4 | 774.1 | 5119.5 | 6150.1 | 5333.1 | 6630.8 |
| 4 | 2 | 717.7 | 450.2 | 2270.2 | 2944.5 | 2306.3 | 2998.3 |
| 5 | 2 | 336.5 | 481.4 | 2443.1 | 3592.3 | 2578.6 | 3828.6 |
| 6 | 2 | 99.8 | 327.4 | 389.3 | 1735.0 | 400.6 | 1798.4 |

Dosing regimen 1 = Day 1 F-I, Day 14 FB
Dosing regimen 2 = Day 1 FB, Day 14 F-I

Surprisingly, based on in vitro solubility and dissolution data, plasma exposure for F-I in terms of area under the concentration versus time curves (AUC) for both 0 to 24 hr and 0 to infinity was significantly higher than that obtained from FB Form 1. Absorption rate did not appear to change as the time to reach Cmax (tmax) ranged from 1 to 2 hours for both FB Form I and F-I. The increased exposure for F-I was most likely due to increased bioavailability, since clearance did not appear to change given the similarities in the apparent half-life of elimination values.

Synthesis

Preparation of FB

Step 1—Stir a mixture of 2-picolyl chloride hydrochloride (7.0 g, 42.7 mmol), 4-piperidone mono-hydrate hydrochloride (6.88 g, 44.8 mmol), powdered sodium carbonate (18.3 g, 173 mmol) and acetonitrile (70 mL) for 45 minutes at ambient temperature, 45 minutes at 40° C., 45 minutes at 50° C., 45 minutes at 60° C., and then heat to 70° C. with vigorous stirring. Monitor the reaction by HPLC (Zorbax RX-C8 25 cm column, acetonitrile/$H_3PO_4$ buffer at pH 3.0, $\lambda$=250 nm) for disappearance of picolyl chloride. At completion of the reaction, allow the mixture to cool to room temperature, filter to remove the insoluble solids, then wash the filter cake with acetonitrile (2×25 ml). Concentrate the filtrate to a small volume (~30 ml) and solvent exchange into 41 ml of ethyl acetate. Rapidly stir and heat the solution to 55° C. then treat, over 30 minutes, with a solution of camphorsulfonic acid (9.91 g, 42.67 mmol) in ethyl acetate (77 mL). Allow the resulting suspension to cool to room temperature then stir for 3 hours. Filter the precipitate, wash with ethyl acetate (2×30 ml), and dry in vacuo at 45° C. to give 15.6 g (87%) of the camphorsulfonic acid salt.

Step 2—To a 1 L 3-neck jacketed vessel under $N_2$, add the product of Step 1 (1.0 equivalent, 33.3.g), 2-(2,2-dimethoxyethyl)aniline (Fukuyama et al, *Tet. Lett.*, 39 (1-2):71-74, 1998; 1.0 equivalent, 14.3 g) and propionic acid (115 mL). Stir the reaction at 20-24° C. until the contents dissolve (15-30 minutes). Cool the mixture to −10 to −15° C., then add 1.0 M NaBH(OPr)$_3$ in tetrahydrofuran (115 mL) over at least 2 hours under $N_2$ while maintaining an internal vessel temperature <−10° C. Confirm completion of the reductive amination by HPLC (Zorbax C-8 column, pH 3.0 (1.5 ml triethylamine/1.5 ml $H_3PO_4$/1 L $H_2O$. Initial gradient: 80% aqueous/20% acetonitrile. Final (45 mins): 20% aqueous/80% acetonitrile). After reaction completion is verified, add ethyl acetate (200 mL) and adjust the reaction temperature to 0° C. Adjust the pH to 10.0 by careful addition of 25% NaOH (315 g) and allow the reaction to warm to 47-52° C. Stir the reaction for 30 minutes to 60 minutes at 47-52° C. Stop stirring the reaction and allow the layers to settle for at least 15 minutes at 47-52° C. Remove the lower aqueous layer and wash the organic layer with aqueous 20% NaCl (150 mL). After stirring for 30 minutes at 47-52° C., stop the agitation and allow the layers to separate over 15 minutes. Remove the lower aqueous layer and reduce the reaction volume to ~65-85 mL by vacuum distillation. Add ethyl acetate (100 mL) back to the reaction and cool the mixture to 23-25° C. Add trifluoroacetic acid (30 ml) over at least 30 minutes. Warm the reaction to 29-31° C. and allow the reaction to proceed until by HPLC analysis the initial amination adduct is present at less than <1.0%. After reaction completion is verified, add ethyl acetate (175 mL) and water (30 mL) and carefully adjust the pH to 9.0 with 25% NaOH (74 g), while warming to 40-45° C. Stir the resultant bi-phasic mixture for at least 1 hour at 45-50° C. and allow the pH to drop to 8.60. Stop the mixing and allow the layers to settle for at least 15 minutes at 45-50° C. Remove the lower aqueous layer and wash the organic layer with aqueous 20% NaCl (125 mL) while stirring at 45-50° C. After 30 minutes stirring, and a 15 minute settle time at 45-50° C., remove the aqueous layer and concentrate the reaction mixture to 100 to 150 mL volume via vacuum distillation. Add isopropanol (400 mL) and concentrate the reaction again to ~200 mL, then add additional isopropanol (200 mL). Concentrate the mixture to ~200 mL final volume via vacuum distillation and age the suspension for 3 hours at 43-45° C., then cool over 3-4 hours to −5° C. Filter the product at −5° C. and wash with pre-cooled (<0° C.) isopropanol (2×40 mL). Dry the reductive amination product at 50-60° C. under reduced pressure.

Step 3—Slurry the product of Step 2 (5.00 g, 17.2 mmol) with dry tert-butyl methyl ether (70 mL, 14 vol.) under $N_2$ at 23° C. Add dry acetonitrile (20 mL, 4 volumes) at ambient temperature in one portion and heat the resulting hazy solution to 40° C. Add a solution of 2.0 M HCl in acetonitrile (8.5 mL, 17.0 mmol, 0.99 equivalent) dropwise over 30 minutes while maintaining a preset jacket temperature of 40° C. Warm the resulting slurry to 50° C. then stir for 1 hour. Cool the mixture to −10° C. over 2-3 hours. Add oxalyl chloride (2.30 mL, 26.4 mmol, 1.50 equivalent) dropwise over 3-5 minutes, keeping the pot temperature <−5° C. Warm the resulting slurry to 0° C. and stir for 1-2 hours until complete reaction by HPLC. Add methanol (10 mL, 2 volumes) dropwise over 3-5 minutes, keeping the pot temperature <10° C. Allow the resulting slurry to gradually warm to 23° C. over 15-30 minutes then stir for 1-2 hours until complete. Cool the slurry to 0-5° C., then add 2N KOH (38 mL, 76 mmol, 4.4 equivalents) dropwise to adjust the pH of the mixture to 7.8 while maintaining the vessel temperature <10° C. Stir the quenched reaction mixture at 10° C. for 15-20 minutes post pH adjustment, then remove the lower aqueous layer. Back-extract the lower aqueous layer with tert-butyl methyl ether (20 mL). Wash the combined organic layers (100 mL) with aqueous 20% NaCl (50 mL) for 20-30 minutes at 10° C. Allow the layers to settle for 15 minutes then remove the brine layer. Subject the organic layer to a body feed of $Na_2SO_4$ (15 g anhydrous), warm to 23° C. then stir for 1-12 hours. Filter the reaction mixture then concentrate the filtrate in vacuo. Re-dissolve the residue in ethyl acetate (100 mL) then re-concentrate. Add ethyl acetate (35 mL) and $CH_3CN$ (1 mL), heat the mixture to 45-50° C. to dissolve, then cool the mixture to 40° C. over an hour. Optionally seed the crude mixture (30 mg) then cool to 23° C. over 2 hours after a suspension forms. Add heptane (80 mL) dropwise over 20-30 minutes to the slurry and then cool the mixture to 0° C. over 1-2 hours. Stir the suspension for an additional 1-2 hours at 0° C. then filter. Rinse the filter cake with cold 2:1/heptane:ethyl acetate (15 mL) then with room temperature heptane (15 mL). Dry the filter cake in a vacuum oven at 50° C. to a constant weight to provide 5.60 g of 1-(1-[(pyridin-2-yl)methyl]piperidin-4-yl)-3-(methoxycarbonylcarbonyl)indole (87%).

Step 4—Charge a 3 neck flask equipped with an addition funnel and nitrogen purge with the product of Step 3 (10.0 grams (1.0 equivalent, 26.5 mmol) and 1-methyl-3-(aminocarbonylmethyl)indole (Faul et al, *J. Org. Chem.*, 63 (17): 6053, 1998; 4.86 g, 0.975 equivalents, 25.8 mmol) in tetrahydrofuran (Karl Ficher <0.03%, 72 ml, 7.2 volumes). Cool the slurry to −5 to −10° C. with an ice/acetone bath. Add potassium t-butoxide (20% in tetrahydrofuran, 1.6 M, 36.4 ml, 2.2 equivalents, 58.3 mmoles) over 10-30 minutes maintaining the reaction temperature at −10 to 5° C. Heat the reaction to 40-45° C. and stir for 1 hour to generate a slurry. Cool the reaction to 0-10° C. with an ice/water bath and then add water (74 mL, pre-chilled to 0-10° C.) rapidly. The reaction generally exotherms to ~15° C. so re-cool the reaction 0-10° C. and adjust the pH to 12.7-12.9 with a mixture of concentrated HCl (5.2 ml) and water (15 ml) (approximately ⅔ of this mixture is required). Adjust the pH with the remainder of the HCl/water mixture over ~20 minutes to a pH of 7.3-7.8 then stir for 30 minutes at 0-10° C. Slowly add water (60 mL) over 20-30 minutes at 0-10° C. and stir the reaction for 1-2 hrs. Filter on a pressure filter and wash with a pre-chilled mixture of tetrahydrofuran (20 ml) and water (60 ml) and dry overnight at 50° C. under vacuum to give FB.

EXAMPLE 1

To a 3 necked flask equipped with heating mantle, condenser and distillate take off add FB (59.0 g, 114.4 mols), 2-butanol (949 ml, 16.1 vols), deionized water (621.4 mL, 10.5 vols) and HCl (food grade: 12.24 mL, 14.13 g, 0.21 volumes, 1.05 equivalents). Heat the reaction to reflux and remove half of the solvent by distillation. Slowly add 2-butanol (27 volumes) over 2 hours, while maintaining a constant solvent level in the reaction flask. Cool the reaction to room temperature over 60 minutes, then cool to 0-5° C. and stir for 1-2 hours. Filter the product and wash the filter cake with 2 volumes of 2-butanol and dry the filter cake overnight at 50° C. under vacuum to give F-I. Elemental Analysis: Theory for $C_{32}H_{30}N_5O_2Cl$: C, 69.62, H, 5.48, N, 12.69, Cl, 6.42; Found: C, 69.29, H, 5.49, N, 12.52, Cl, 6.54.

XRD patterns were obtained on a Siemens D5000 X-ray powder diffractometer, equipped with a CuKα source ($\lambda$=1.54056 Å) and a Kevex solid-state detector, operating at 50 kV and 40 mA with a 1 mm divergence and receiving slit and 0.1 mm detector slit. Each sample was scanned between 4° and 35° in 2θ with a step size of 0.020 and a maximum scan rate of 3 sec/step. The XRD pattern for the material produced in Example 1 is as described in Table 1 and FIG. 1.

Formulation

A salt of the present invention is preferably formulated in a unit dosage form prior to administration. Therefore, yet another embodiment of the present invention is a pharmaceutical composition comprising a salt of the present invention and a pharmaceutical carrier. The term "pharmaceutical" when used herein as an adjective means substantially non-deleterious to the recipient patient.

The present pharmaceutical compositions are prepared by known procedures using well-known and readily available ingredients. In making the formulations of the present invention, the active ingredient (e.g., F-I) will usually be mixed with a carrier, or diluted by a carrier, or enclosed within a carrier that may be in the form of a capsule, sachet, paper or other container. When the carrier serves as a diluent, it may be a solid, semisolid or liquid material that acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Formulation Example 1

25 mg Capsule

| Ingredient | Quantity (mg/capsule) |
| --- | --- |
| F-I | 27.1 |
| Crospovidone XL | 16.9-24.4 |
| Lactose Anhydrous | 142.2-164.4 |
| Lactose Monohydrate | 142.2-164.4 |
| Magnesium Stearate Vegetable | 1.1-2.8 |
| Povidone | 13.1-16.9 |
| Polysorbate 80 | 1.9-5.6 |

Formulation Example 2

100 ml Capsule

| Ingredient | Quantity (mg/capsule) |
| --- | --- |
| F-I | 108.5 |
| Crospovidone XL | 16.9-24.4 |
| Lactose Anhydrous | 101.5-123.8 |
| Lactose Monohydrate | 101.5-123.8 |
| Magnesium Stearate Vegetable | 1.1-2.8 |
| Povidone | 13.1-16.9 |
| Polysorbate 80 | 1.9-5.6 |

The capsules above are manufactured by an aqueous granulation process, as described below. The lactose, a portion of the crospovidone, and the active ingredient (F-I) are added to the granulator and dry blended for a suitable period of time to uniformly distribute the powders. A granulation solution consisting of povidone and polysorbate 80 in purified water is sprayed at a uniform rate onto the powders while mixing under specified conditions. When a suitable granulation endpoint is reached, the granulator is stopped and the granulation is unloaded.

The granulation is wet sieved through a suitable screen to disrupt large agglomerates, spread on paper lined trays, and dried in a convection oven until the moisture is reduced to a suitable level. The size of the granulation is reduced to a desirable range by passing through a co-mill or other suitable apparatus. These sized powders are collected, transferred to a mixing apparatus, and blended with a specified quantity of magnesium stearate and additional crospovidone until uniformly distributed. The finished powders are then filled into hard gelatin capsules either manually or on a suitable piece of automated capsule filling equipment.

Following the filling operation, the finished capsules are visually inspected for external defects. To improve the pharmaceutical elegance of the finished product, the capsules may be physically de-dusted and polished by either manual or automated processes.

Demonstration of Function

The salt of the present invention is an inhibitor of vascular endothelial growth factor (VEGF)-induced angiogenesis. At least two assay systems demonstrate these pharmacologic activities: 1) F-I is a potent inhibitor of VEGF-stimulated proliferation of HUVEC cells in culture upon 72 hours of exposure to the compound; 2) F-I is a highly effective inhibitor of VEGF-induced neo-angiogenesis in the rat corneal micropocket when administered orally to the animals for 10 days. These assay systems are more fully described in WO 02/02116. The salt of the present invention is, thus, effective in treating cancer and inhibiting tumor growth.

Utilities

As tumor growth inhibitors, the salt of the present invention is useful to treat cancers of the bladder, brain, breast, cervix, colorectum, esophagus, kidney, head and neck, liver, lung, ovaries, pancreas, prostate and stomach. The salt of the present invention is also useful to treat soft tissue sarcomas and osteosarcomas and to treat Hodgkins and non-Hodgkins lymphoma or hematological malignancies (leukemias).

Preferred methods of using a salt of the present invention relate to its use to treat cancers of the bladder, kidney, brain, breast, colorectum, liver, lung (non-small cell), ovaries and stomach and to its use to treat non-Hodgkins lymphoma (e.g., diffuse large B cell and mantle cell lymphoma) or hematological malignancies (leukemias).

Even more preferred methods of using a salt of the present invention relate to its use to treat cancers of the brain, colorectum, lung (non-small cell), and to its use to treat non-Hodgkins lymphoma, β cell lymphomas and β cell related leukemias.

Dose

One skilled in the art will recognize that the amount of a salt of the present invention to be administered in accordance with the present invention, that is, a therapeutically effective amount, is that amount sufficient to produce an anti-neoplastic effect, to induce apoptosis or cell death, and/or to maintain an antiangiogenic effect.

Generally, an amount of a salt of the present invention to be administered is decided on a case-by-case basis by the attending physician. As a guideline, the extent and type of the neoplasia, the timing of administration relative to other therapies (if any), and the body weight, and age of the patient will be considered, among other factors, when setting an appropriate dose. Typically, an effective minimum daily dose of a salt of the present invention, e.g., F-I, will exceed about 200 mg (usually >400 mg, e.g., 500 mg). Usually, an effective maximum daily dose of F-I will not exceed about 700 mg. However, in the case of glioblastomas (brain tumors) the maximum daily dose of F-I could be as high as 1400 mg. The exact glioblastoma dose may be determined, in accordance with the standard practice in the medical arts of "dose titrating" the recipient; that is, initially administering a low dose of the compound, e.g., 200 or 400 mg and gradually increasing the dose until the desired therapeutic effect is observed.

Route of Administration

The salt of the present invention can be administered by a variety of routes including the oral, rectal, transdermal, subcutaneous, topical, intravenous, intramuscular or intranasal routes. The oral route is preferred.

Combination Therapy

The salt of the present invention may be used in combination with conventional anti-neoplasm therapies to treat mammals, especially humans, with neoplasia. The procedures for conventional anti-neoplasm therapies, including chemotherapies using anti-neoplastic agents and therapeutic radiation, are readily available, and routinely practiced in the art, e.g., see Harrison's PRINCIPLES OF INTERNAL MEDICINE 11th edition, McGraw-Hill Book Company.

Specifically, a crystalline salt of the present invention may be used to enhance the anti-neoplasm effects of an anti-neoplastic agent. A wide variety of available anti-neoplastic agents are contemplated for combination therapy in accordance with present invention.

Anti-neoplastic agents contemplated for combination therapy in accordance with the present invention include, but are not limited to: alkylating agents, including busulfan, chlorambucil, cyclophosphamide, ifosfamide, melphalan, nitrogen mustard, streptozocin, thiotepa, uracil nitrogen mustard, and triethylenemelamine, temozolomnide; antibiotics and plant alkaloids including actinomycin-D, bleomycin, cryptophycins, daunorubicin, doxorubicin, idarubicin, irinotecan, L-asparaginase, mitomycin-C, mithramycin, navelbine, paclitaxel, docetaxel, topotecan, vinblastine, vincristine, and VP-16; hormones and steroids including aminoglutethimide, anastrozole, bicalutamide, DES, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, tamoxifen, testosterone and triamicnolone; synthetics including all-trans retinoic acid, BCNU (carmustine), carboplatin (paraplatin), CCNU (lomustine), cis-diaminedichloroplatinum (cisplatin), dacarbazine, hexamethylmelamine, hydroxyurea, levamisole, mitoxantrone, oxaliplatin, procarbazine; antimetabolites including chlorodeoxyadenosine, cytosine arabinoside, 2'-deoxycoformycin, fludarabine phosphate, 5-fluorouracil, 5-FUDR, gemcitabine, 6-mercaptopurine, methotrexate, pemetrexed, and thioguanine; monoclonal antibodies including rituximab and trastuzumab; antisense compounds including ISIS 3521; and biologics including alpha interferon, BCG, G-CSF, GM-CSF, and interleukin-2; and the like. These anti-neoplastic agents assert their cytotoxicity or anti-neoplasm effects in a variety of specific neoplastic conditions (see WO 02/02094).

In a preferred embodiment of the invention one or more anti-neoplastic agents are selected from the group consisting of BCNU, cyclophosphamide, doxorubicin, prednisone or dexamethasone, vincristine, gemcitabine, cisplatin, 5 fluorouracil, capecitibine, CPT-11, carboplatin, paclitaxel, docetaxel, rituximab and trastuzumab.

A crystalline salt of the present invention may also be used in combination with radiation therapy. Usually, radiation is used to treat the site of a solid tumor directly or administered by brachytherapy implants.

Therapeutic radiation contemplated for combination therapy in accordance with the present invention are those used in the treatment of cancer which include, but are not limited to X-rays, gamma radiation, high energy electrons and High LET (Linear Energy Transfer) radiation such as protons, neutrons, and alpha particles. The ionizing radiation is employed by techniques well known to those skilled in the art. For example, X-rays and gamma rays are applied by external and/or interstitial means from linear accelerators or radioactive sources. High-energy electrons can be produced by linear accelerators. High LET radiation is also applied from radioactive sources implanted interstitially.

The phrase "in combination with" means that the crystalline salt of the present invention is administered shortly before, shortly after, concurrently, or any combination of before, after, or concurrently, with such other anti-neoplasm therapies. A salt of the present invention may be administered in combination with more than one anti-neoplasm therapy. In a preferred embodiment, the a salt of the present invention is administered from 2 weeks to 1 day before any chemotherapy, or 2 weeks to 1 day before any radiation therapy. In another preferred embodiment, a salt of the present invention may be administered during anti-neoplastic chemotherapies and radiation therapies. If administered following such chemotherapy or radiation therapy, a salt of the present invention is preferably given within 1 to 14 days following the primary treatments. A salt of the present invention may also be administered chronically or semi-chronically, over a period of from about 2 weeks to about 5 years.

We claim:

1. A crystalline 2,5-dione-3-(1-methyl-1H-indol-3-yl)-4-[1-(pyridin-2-ylmethyl)piperidin-4-yl]-1H-indol-3-yl]-1H-pyrrole mono-hydrochloride or a hydrate thereof containing up to and including 1.6% water having an X-ray diffraction pattern which comprises the following peaks: 6.8±0.1, 10.9±0.1, 14.2±0.1 and 16.6±0.1° in 2θ; when the pattern is obtained from a copper radiation source (CuKα; λ=1.54056 Å).

2. A pharmaceutical composition comprising the crystalline mono-hydrochloride or the hydrate thereof of claim 1 and a pharmaceutical carrier.

* * * * *